(12) United States Patent
Caruel et al.

(10) Patent No.: US 10,501,434 B2
(45) Date of Patent: Dec. 10, 2019

(54) CONFIGURATIONAL STEREOISOMER OF DIFETHIALONE, COMPOSITION AND RODENTICIDAL BAIT COMPRISING SAME, AND PROCESS FOR CONTROLLING TARGET RODENT PESTS

(71) Applicants: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy l'Etoile (FR)

(72) Inventors: Hervé Caruel, Moncaut (FR); Etienne Benoit, Lyons (FR); Isabelle Fourel, Miribel (FR); Virginie Lattard, Lyons (FR)

(73) Assignees: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy l'Etoile (FR)

( * ) Notice: Subject to any disclaimer, the term of this patent is extended or adjusted under 35 U.S.C. 154(b) by 0 days.

(21) Appl. No.: 16/061,084

(22) PCT Filed: Dec. 6, 2016

(86) PCT No.: PCT/EP2016/079858
§ 371 (c)(1),
(2) Date: Jun. 11, 2018

(87) PCT Pub. No.: WO2017/097747
PCT Pub. Date: Jun. 15, 2017

(65) Prior Publication Data
US 2018/0362494 A1 Dec. 20, 2018

(30) Foreign Application Priority Data
Dec. 11, 2015 (FR) ..... 15 62230

(51) Int. Cl.
C07D 335/06 (2006.01)
A01N 43/18 (2006.01)
A01N 25/00 (2006.01)
B01D 15/38 (2006.01)

(52) U.S. Cl.
CPC ......... *C07D 335/06* (2013.01); *A01N 25/004* (2013.01); *A01N 43/18* (2013.01); *B01D 15/3833* (2013.01); *C07B 2200/07* (2013.01)

(58) Field of Classification Search
CPC .................................................. C07D 335/06
See application file for complete search history.

(56) References Cited

U.S. PATENT DOCUMENTS

| 4,585,786 A | 4/1986 | Berthelon |
| 4,783,481 A | 11/1988 | Swaine |
| 2005/0181003 A1 | 8/2005 | Endepols et al. |

FOREIGN PATENT DOCUMENTS

| EP | 0147052 A2 | 7/1985 |
| EP | 0161163 A1 | 11/1985 |
| EP | 2090164 B1 | 12/2011 |
| WO | 2015189321 A1 | 12/2015 |

OTHER PUBLICATIONS

International Search Report, dated Jan. 23, 2017, from corresponding PCT application No. PCT/EP2016/079858.
Koubek, K. G., J. P. Ussary, and R. E. Haulsee. "High pressure liquid chromatographic determination of the rodenticide brodifacoum in rat tissue." Journal-Association of Official Analytical Chemists 62.6 (1979): 1297-1301.

*Primary Examiner* — Brian J Davis
(74) *Attorney, Agent, or Firm* — Ipsilon USA, LLP (57) ABSTRACT

Disclosed is to a laevorotatory enantiomer of the configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations.

20 Claims, 5 Drawing Sheets

CONFIGURATIONAL STEREOISOMER OF DIFETHIALONE, COMPOSITION AND RODENTICIDAL BAIT COMPRISING SAME, AND PROCESS FOR CONTROLLING TARGET RODENT PESTS

The invention relates to a configurational stereoisomer of difethialone, to a composition and a rodenticidal bait comprising such a configurational stereoisomer and to a process for controlling target rodent pests. The invention thus relates to the technical field of controlling populations of target rodent pests.

It is known practice to use rodenticidal baits as poisons for target rodent pests. It is known from EP 2 090 164 that difethialone is a second-generation anticoagulant acting in a single dose. US 2005/181003 describes a rodenticidal bait in gel form comprising difethialone in a mass proportion of 25 ppm.

Such a bait is liable to be consumed by animals other than target rodent pests when it is made available to target rodent pests. It may be consumed directly (primary consumption) by domestic animals or pets. It may also be consumed accidentally by humans. Such consumption may result in poisoning, which may be lethal, of these domestic animals, pets or humans.

In addition, a fraction of the difethialone of these rodenticidal baits may be ingested (secondary consumption) by animals—especially by birds—which prey on weakened rodent pests that have consumed such a rodenticidal bait, or by animals which carrion-feed on rodent pests that have died from having consumed such a rodenticidal bait. This secondary consumption is liable in the long term to result in the death of these predatory or carrion-feeding animals, which may be animals—especially birds—belonging to protected species.

The invention is thus directed towards overcoming these drawbacks by proposing a configurational stereoisomer of difethialone, a composition and a rodenticidal bait comprising such a configurational stereoisomer and a process for controlling target rodent pests, which are effective for controlling the populations of target rodent pests and can also limit the risks of poisoning of non-target animals—especially domestic animals, pets or humans—accidentally consuming such a rodenticidal bait and the risks of poisoning of domestic animals (pets or reared animals) or wild animals—for example foxes or birds—which prey on weakened target rodent pests which have consumed the rodenticidal bait or which carrion-feed on target rodent pests that have died from being poisoned by consumption of such a rodenticidal bait.

The invention is also directed towards proposing a configurational stereoisomer of difethialone, a composition and a rodenticidal bait comprising such a configurational stereoisomer and a process for controlling target rodent pests, the use of which is in accordance with the rules of good practice, especially with respect to the protection of birds, and in particular birds of prey.

The invention is also directed towards proposing a configurational stereoisomer of difethialone, a composition and a rodenticidal bait comprising such a configurational stereoisomer and a process for controlling target rodent pests, which do not require, in order to control a population of target rodent pests, the use of massive doses of a rodenticidal agent and which are friendly towards the environment and the health of humans and non-target animals—especially birds.

The invention is also directed towards proposing a configurational stereoisomer of difethialone, a composition and a rodenticidal bait comprising such a configurational stereoisomer and a process for controlling target rodent pests, which are able to be used for controlling target rodent pests that have become resistant to known baits for controlling target rodent pests.

The invention is thus directed towards proposing an alternative to known rodenticidal baits.

To do this, the invention relates to a laevorotatory enantiomer of a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations.

Throughout the text:
   the term "difethialone" denotes the compound 3-(4'-bromobiphenyl-4-yl)-1-(4-hydroxythiocoumarin-3-yl)-1,2,3,4-tetrahydronaphthalene or 3-[3-[4-(4-bromophenyl)phenyl]-1-tetralinyl]-2-hydroxy-4-thiochromenone or 3-[3-(4'-bromo[1,1'-biphenyl]-4-yl)-1,2,3,4-tetrahydro-1-naphthalenyl]-4-hydroxy-2H-1-benzothiopyran-2-one of formula (I) below:

in which the numbers of carbons 1 and 3 of the 1,2,3,4-tetrahydronaphthalene group are indicated;
   the term "stereoisomers" denotes isomers of the same semi-structural formula, but in which the relative position of the atoms differs in space. The term "configurational stereoisomers" denotes stereoisomers for which conversion from one to the other of these configurational stereoisomers requires the cleavage/reformation of an interatomic covalent bond. Thus, the term "configurational stereoisomers" denotes stereoisomers which are not conformational isomers (or "rotamers", for which conversion from one to the other of the conformational isomers is accompanied only by rotation of a part of the molecule about the axis of a σ (sigma) bond formed by axial orbital overlap);
   the term "hetero-stereoisomer" of difethialone denotes the configurational stereoisomer of difethialone of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said hetero-stereoisomer have different absolute configurations (1R,3S and 1S,3R), said absolute configurations being determined according to the sequential priority rules and the Cahn-Ingold-Prelog (CIP) nomenclature;
   the term "homo-stereoisomer" of difethialone denotes the configurational stereoisomer of difethialone of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said homo-stereoisomer have the same absolute configuration (1R,3R and 1S,3S);

the term "amount" means a molar amount, a mass amount or a volume amount. The proportions are thus proportions of a molar amount relative to a molar amount, of a mass amount relative to a mass amount, or of a volume amount relative to a volume amount;

the term "substantially" indicates, in the usual manner, that a structural or functional characteristic should not be taken as marking an abrupt discontinuity, which would have no physical meaning, but covers not only this structure or this function, but also slight variations of this structure or of this function which produce, in the technical context under consideration, an effect of the same nature, or else of the same degree;

the expressions "high-pressure liquid chromatography" or "high-performance liquid chromatography" (HPLC) denote "HPLC" chromatography or "High-Performance Liquid Chromatography"; and the term "retention time" denotes the time, measured at the top of the peak in the chromatogram, for which a compound is retained on a chromatography column.

The invention relates to the laevorotatory enantiomer of said hetero-stereoisomer of difethialone. The invention relates to the laevorotatory enantiomer of said hetero-stereoisomer of difethialone in isolated form and in particular separated from the dextrorotatory enantiomer of said hetero-stereoisomer of difethialone and from the laevorotatory and dextrorotatory enantiomers of a configurational stereoisomer of difethialone, named homo-stereoisomer, in which carbons 1 and 3 of the 1,2,3,4-tetrahydronaphthalene group have the same absolute configuration.

The inventors have discovered that it is possible to separate the laevorotatory and dextrorotatory enantiomers of said hetero-stereoisomer of difethialone and the laevorotatory and dextrorotatory enantiomers of said homo-stereoisomer of difethialone by high-pressure liquid chromatography in isocratic mode and under particular conditions by using a chromatography column comprising a chiral stationary phase. Specifically, it was not known at the date of the invention how to separate the laevorotatory and dextrorotatory enantiomers of said hetero-stereoisomer of difethialone and of said homo-stereoisomer of difethialone.

The inventors succeeded in performing this separation by using a LUX® Cellulose-3 HPLC column (Phenomenex, Le Pecq, France) of dimensions 150×2 mm and comprising a chiral stationary phase constituted of porous particles of tris(4-methylbenzoate) cellulose, having a particle size of 3 m and a porosity of 1000 Å. The inventors used, as mobile phase, an eluent obtained by mixing acetonitrile (A) and water comprising formic acid in a volume proportion of 0.1% in the water (B) with an A/B volume ratio of 80/20. The flow rate of the mobile phase in the column is maintained at a value of 0.25 mL/minute and the separation is performed at a temperature of 23.2° C. The composition to be analysed is at a concentration of 1 μg of difethialone per millilitre in acetonitrile and the volume of composition injected onto the column is 1 μL. Detection may be performed by tandem mass spectrometry (MS/MS). Detection may also be performed by photometry or by spectrophotometry by adjusting the difethialone concentration and the injection volume for the purpose of obtaining optimum detection and by measuring the value of the area under the peak for each enantiomer.

Under these experimental conditions, the value of the retention time ($t_2$) for the laevorotatory enantiomer of said hetero-stereoisomer of difethialone according to the invention may vary according to the operating conditions—especially according to the column temperature conditions—and may be between 9.0 minutes and 9.5 minutes. The value of the retention time ($t_3$) for the dextrorotatory enantiomer of said hetero-stereoisomer of difethialone may vary according to the operating conditions—especially according to the column temperature conditions—and may be between 11.3 minutes and 11.8 minutes, such that the dextrorotatory and laevorotatory enantiomers of said hetero-stereoisomer may be separated by high-pressure liquid chromatography on this chiral column.

The value of the retention time ($t_1$) for the laevorotatory enantiomer of said homo-stereoisomer may vary according to the operating conditions—especially according to the column temperature conditions—and may be between 7.8 minutes and 8.2 minutes. The value of the retention time ($t_4$) for the dextrorotatory enantiomer of said homo-stereoisomer according to the invention may vary according to the operating conditions—especially according to the column temperature conditions—and may be between 14.0 minutes and 14.4 minutes, such that the dextrorotatory and laevorotatory enantiomers of said homo-stereoisomer may be separated by high-pressure liquid chromatography on a chiral column.

Thus, under these analytical conditions, the order of elution of the configurational stereoisomers of difethialone is such that $t_1 < t_2 < t_3 < t_4$. The retention time values $t_1$, $t_2$, $t_3$ and $t_4$ are liable to vary, especially with the temperature of the chromatography column. However, under these chromatographic conditions, the order of elution of the configurational stereoisomers of difethialone remains unchanged.

The invention thus relates to the laevorotatory enantiomer of said hetero-stereoisomer of difethialone in isolated form and having the property of being able to be eluted, under the chromatography conditions described above, second from among the four configurational stereoisomers of difethialone.

The laevorotatory enantiomer of said hetero-stereoisomer of difethialone isolated in pure form according to the invention, dissolved in methanol at a concentration of 0.94 g/L and placed in a quartz spectrophotometry cuvette, has a circular dichroism spectrum acquired at 25° C. with negative circular dichroism values between 225 nm and 250 nm.

The laevorotatory enantiomer of said hetero-stereoisomer of difethialone isolated in pure form according to the invention, dissolved in chloroform ($CHCl_3$), has a specific optical rotation $[\alpha]^{25°\ C.}_{589nm}$, measured at 25° C. and on the sodium D line (589 nm), having a value of −13°.

The laevorotatory enantiomer of said hetero-stereoisomer of difethialone isolated in pure form according to the invention has, on proton magnetic resonance ($^1$H-NMR) spectroscopy at 500 MHz in $CDCl_3$, a multiplet with a chemical shift (δ) of about 5.3 ppm corresponding to the proton borne by carbon 1 of the 1,2,3,4-tetrahydronaphthalene group of said hetero-stereoisomer of difethialone.

Said hetero-stereoisomer of difethialone and said homo-stereoisomer of difethialone are distinguished by their proton NMR spectra. In a proton NMR spectrum acquired in $CDCl_3$, the chemical shift of the proton borne by carbon 1 of the 1,2,3,4-tetrahydronaphthalene group of said homo-stereoisomer of difethialone is between 4.9 ppm and 5.1 ppm.

The invention also relates to a composition comprising the laevorotatory enantiomer of said hetero-stereoisomer of difethialone according to the invention, with the exclusion of a racemic mixture of laevorotatory and dextrorotatory enantiomers of said hetero-stereoisomer of difethialone.

The invention thus also relates to a composition comprising a laevorotatory enantiomer of a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations, with the exclusion of a racemic mixture of the laevorotatory and dextrorotatory enantiomers of said hetero-stereoisomer of difethialone, i.e. with the exclusion of a composition in which the laevorotatory enantiomer of said hetero-stereoisomer of difethialone is in a racemic (equimolar) mixture with the dextrorotatory enantiomer of said hetero-stereoisomer of difethialone.

The invention thus relates to such a composition in which the laevorotatory enantiomer of said hetero-stereoisomer of difethialone and the dextrorotatory enantiomer of said hetero-stereoisomer of difethialone are in unequal (different) amounts.

Advantageously and according to the invention, said hetero-stereoisomer is predominantly in the laevorotatory enantiomer form of said hetero-stereoisomer of difethialone. Advantageously, a composition according to the invention comprises said hetero-stereoisomer of difethialone predominantly in laevorotatory enantiomer form. The invention thus relates to a composition in which said hetero-stereoisomer of difethialone is predominantly in laevorotatory enantiomer form.

Throughout the text hereinbelow, the term "said hetero-stereoisomer is predominantly in laevorotatory enantiomer form" means that the (mass, molar or volume) amount of laevorotatory enantiomer of said hetero-stereoisomer of difethialone is in major amount—greater than 50%—in the total amount of said hetero-stereoisomer of difethialone present in the composition (in all its dextrorotatory and laevorotatory enantiomer forms).

Advantageously and according to the invention, the composition comprises an amount of the laevorotatory enantiomer of said hetero-stereoisomer of difethialone such that the ratio of this amount to the amount of said hetero-stereoisomer of difethialone is greater than 50%, especially greater than 60%, in particular greater than 70%, more particularly greater than 80%, preferably greater than 90%, more preferentially greater than 95%, particularly preferentially greater than 98%, even more preferentially greater than 99% or about 100%. Advantageously, the composition comprises an amount of the laevorotatory enantiomer of said hetero-stereoisomer of difethialone such that the ratio of this amount to the amount of said hetero-stereoisomer of difethialone is greater than 75%, preferably between 85% and 100%, more preferentially between 90% and 98%. Advantageously, the composition comprises an amount of the laevorotatory enantiomer of said hetero-stereoisomer of difethialone such that the ratio of this amount to the amount of said hetero-stereoisomer of difethialone is between 98% and 100%.

The invention thus relates to a composition in which said hetero-stereoisomer of difethialone is predominantly in laevorotatory enantiomer form.

In particular, in a composition according to the invention:
the ratio of the amount of laevorotatory enantiomer of said hetero-stereoisomer of difethialone to the sum of the amounts of each of the (laevorotatory and dextrorotatory) enantiomers of said hetero-stereoisomer of difethialone is greater than 0.5 (greater than 50%);
the ratio of the concentration of laevorotatory enantiomer of said hetero-stereoisomer of difethialone to the sum of the concentrations of each of the (laevorotatory and dextrorotatory) enantiomers of said hetero-stereoisomer of difethialone is greater than 0.5 (greater than 50%); and
the proportion of laevorotatory enantiomer of said hetero-stereoisomer of difethialone in the composition is greater than the proportion of the dextrorotatory enantiomer of said hetero-stereoisomer of difethialone. In a composition according to the invention, the proportion of laevorotatory enantiomer of said hetero-stereoisomer of difethialone in the composition is more than 50% relative to said hetero-stereoisomer of difethialone.

Advantageously, the composition may also comprise an amount of dextrorotatory enantiomer of said hetero-stereoisomer of difethialone such that the ratio of this amount to the amount of said hetero-stereoisomer of difethialone in the composition is less than 50%, especially less than 25%, preferentially between 0% and 25%, in particular less than 10%.

Advantageously and according to the invention, the difethialone is predominantly in the laevorotatory enantiomer form of said hetero-stereoisomer of difethialone. The composition comprises the laevorotatory enantiomer of said hetero-stereoisomer of difethialone in a proportion greater than each of the proportions of each of the other enantiomers of difethialone relative to the difethialone in the composition.

Advantageously, in a composition according to the invention:
the ratio of the amount of laevorotatory enantiomer of said hetero-stereoisomer of difethialone to the sum of the amounts of each of the (laevorotatory and dextrorotatory) enantiomers of said hetero-stereoisomer of difethialone and of the amount of said homo-stereoisomer of difethialone is greater than 0.25 (greater than 25%);
the ratio of the concentration of laevorotatory enantiomer of said hetero-stereoisomer of difethialone to the sum of the concentrations of each of the (laevorotatory and dextrorotatory) enantiomers of said hetero-stereoisomer of difethialone and of the concentration of said homo-stereoisomer of difethialone is greater than 0.25 (greater than 25%); and
the proportion of laevorotatory enantiomer of said hetero-stereoisomer of difethialone in the composition is greater than the proportion of each of the enantiomers of said homo-stereoisomer of difethialone and of the other enantiomer of said hetero-stereoisomer of difethiazone. In a composition according to the invention, the proportion of laevorotatory enantiomer of said hetero-stereoisomer of difethialone in the composition is more than 25% relative to the total difethialone.

Advantageously and according to the invention, the composition comprises an amount of the laevorotatory enantiomer of said hetero-stereoisomer of difethialone such that the ratio of this amount to the (total) amount of difethialone is greater than 25%, especially greater than 50%, in particular greater than 70%, more particularly greater than 80%, preferably greater than 90%, particularly preferentially greater than 95%, more preferentially greater than 98%, even more preferentially greater than 99% or about 100%. A composition according to the invention thus comprises difethialone predominantly in the laevorotatory enantiomer form of said hetero-stereoisomer of difethialone.

Advantageously, the composition comprises an amount of the laevorotatory enantiomer of said hetero-stereoisomer of difethialone such that the ratio of this amount to the (total) amount of difethialone is greater than 70%, preferably between 80% and 100%, more preferentially between 90% and 100%. Advantageously, the composition comprises an amount of the laevorotatory enantiomer of said hetero-stereoisomer of difethialone such that the ratio of this amount to the (total) amount of difethialone is between 95% and 99%. Advantageously, the composition comprises an amount of the laevorotatory enantiomer of said hetero-stereoisomer of difethialone such that the ratio of this amount to the (total) amount of difethialone is between 98% and 100%. Advantageously, the composition comprises an amount of the laevorotatory enantiomer of said hetero-stereoisomer of difethialone such that the ratio of this amount to the (total) amount of difethialone is substantially about 100%.

Advantageously and according to the invention, the composition comprises an amount of the laevorotatory enantiomer of said hetero-stereoisomer of difethialone such that the ratio of this amount to the (total) amount of difethialone is greater than 97% relative to the difethialone.

A composition according to the invention may be substantially free of dextrorotatory enantiomer of said hetero-stereoisomer of difethialone, i.e. the dextrorotatory enantiomer of said hetero-stereoisomer of difethialone may be present in the composition, but only in trace amount. The composition may also be substantially free of the configurational stereoisomer, named homo-stereoisomer, of difethialone in which carbons 1 and 3 of the 1,2,3,4-tetrahydronaphthalene group have the same absolute configuration, i.e. said homo-stereoisomer of difethialone may be present in the composition, but only in trace amount.

Advantageously and according to the invention, the composition is in liquid form and comprises a liquid solvent for difethialone. It may be a solution of difethialone in a solvent for difethialone, with the exclusion of a racemic mixture of said laevorotatory and dextrorotatory enantiomers of said hetero-stereoisomer of difethialone. It may also be a solution comprising difethialone in a solvent for difethialone and in which said hetero-stereoisomer of difethialone is predominantly in laevorotatory enantiomer form. It may also be a solution comprising difethialone in a solvent for difethialone and in which the difethialone is predominantly in the laevorotatory enantiomer form of said hetero-stereoisomer of difethialone. It may also be a suspension or an emulsion of difethialone in a liquid medium.

Advantageously and according to the invention, the composition is in solid form. It may also be a solid comprising difethialone, with the exclusion of a racemic mixture of the dextrorotatory and laevorotatory enantiomers of said hetero-stereoisomer of difethialone. It may also be a solid comprising difethialone and in which said hetero-stereoisomer of difethialone is predominantly in laevorotatory enantiomer form. It may also be a solid comprising difethialone and in which the difethialone is predominantly in the laevorotatory enantiomer form of said hetero-stereoisomer of difethialone.

The invention thus also relates to a composition comprising difethialone, the difethialone of the composition being optically active. However, it is not excluded for the difethialone of the composition according to the invention to be optically inactive.

The invention also relates to the use of a composition according to the invention for the preparation of a rodenticidal bait for target rodent pests.

The invention also relates to a rodenticidal bait comprising a composition according to the invention, and at least one excipient that is edible for target rodent pests.

A rodenticidal bait according to the invention comprises: at least one excipient that is edible for target rodent pests, the laevorotatory enantiomer of the configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations, with the exclusion of a racemic mixture of laevorotatory and dextrorotatory enantiomers of said hetero-stereoisomer of difethialone. In a rodenticidal bait according to the invention, the amount of laevorotatory enantiomer of said hetero-stereoisomer of difethialone is different from the amount of dextrorotatory enantiomer of said hetero-stereoisomer of difethialone.

The inventors, who succeeded in separating the dextrorotatory enantiomer of said hetero-stereoisomer of difethialone and the laevorotatory enantiomer of said hetero-stereoisomer of difethialone and in obtaining the laevorotatory enantiomer of said hetero-stereoisomer of difethialone in isolated form, also observed, entirely surprisingly, that the laevorotatory enantiomer of said hetero-stereoisomer of difethialone and the dextrorotatory enantiomer of said hetero-stereoisomer of difethialone do not have the same hepatic persistence in target rodent pests and that the laevorotatory enantiomer of said hetero-stereoisomer of difethialone is in fact the enantiomer of said hetero-stereoisomer of difethialone which has the lower hepatic persistence in target rodents, especially in target rodent pests.

Even more unexpectedly, they observed that, although said hetero-stereoisomer of difethialone has higher hepatic persistence than said homo-stereoisomer of difethialone, the laevorotatory enantiomer of said hetero-stereoisomer of difethialone in fact has low hepatic persistence, and in any case lower than that of the dextrorotatory enantiomer of said hetero-stereoisomer of difethialone, lower than that of said hetero-stereoisomer of difethialone and lower than that of difethialone itself.

They observed that the laevorotatory enantiomer of said hetero-stereoisomer of difethialone, when ingested by a target rodent pest, is less persistent and disappears from the liver of the target rodent pest which has consumed a bait according to the invention more rapidly than the disappearance of the dextrorotatory enantiomer of said hetero-stereoisomer of difethialone. The residual amount of laevorotatory enantiomer of said hetero-stereoisomer of difethialone in the body of a poisoned rodent decreases more rapidly than the amount of the dextrorotatory enantiomer of said hetero-stereoisomer of difethialone. The dead or live target rodent pest which has ingested beforehand the laevorotatory enantiomer of said hetero-stereoisomer of difethialone is less toxic with respect to non-rodent mammals and birds which consume the target rodent pest—dead or alive—and in particular with respect to predators (especially non-rodent mammals and birds) which preferentially consume the viscera of their prey and in particular their liver.

The inventors have also observed that the laevorotatory enantiomer of said hetero-stereoisomer of difethialone, although having lower hepatic persistence in target rodent pests, does in fact make it possible, in an entirely surprising manner, to efficiently control target rodent pests.

The laevorotatory enantiomer of said hetero-stereoisomer of difethialone constitutes a choice candidate for controlling populations of target rodent pests that have become resistant to known rodenticidal treatments.

Advantageously and according to the invention, the rodenticidal bait may comprise an excipient that is edible for target rodent pests and said hetero-stereoisomer of difethialone predominantly in the laevorotatory enantiomer form of said hetero-stereoisomer of difethialone. Advantageously and according to the invention, the rodenticidal bait may comprise an excipient that is edible for target rodent pests and difethialone predominantly in the laevorotatory enantiomer form of said hetero-stereoisomer of difethialone.

Advantageously and according to the invention, the rodenticidal bait comprises a mass amount of difethialone such that the ratio (mass proportion) of this mass amount of difethialone to the mass amount of rodenticidal bait is less than 200 ppm, i.e. less than 200 mg of difethialone per kilogram of bait. Advantageously, the mass proportion of difethialone in the rodenticidal bait is between 1 ppm and 100 ppm (1 mg to 100 mg of difethialone per kilogram of rodenticidal bait), especially between 5 ppm and 100 ppm (5 mg to 100 mg of difethialone per kilogram of rodenticidal bait), preferably between 5 ppm and 50 ppm (5 mg to 50 mg of difethialone per kilogram of rodenticidal bait), more preferentially between 10 ppm and 50 ppm (10 mg to 50 mg of difethialone per kilogram of rodenticidal bait), even more preferentially between 15 ppm and 50 ppm (15 mg to 50 mg of difethialone per kilogram of rodenticidal bait), for example about 15 ppm (15 mg of difethialone per kilogram of bait).

Advantageously and according to the invention, the excipient that is edible for target rodent pests is chosen to allow consumption of the bait by target rodent pests. Advantageously and according to the invention, each edible excipient is non-lethal to target rodent pests. The edible excipient is not in itself rodenticidal.

Advantageously and according to the invention, the edible excipient comprises at least one food chosen from the group formed by cereal seeds, especially hulled cereal seeds, cereal seed meals, cereal seed flours, cereal seed flakes, cereal bran and non-cereal seeds, for example alfalfa seeds, especially in hulled form, in the form of meal, in the form of flour, or in the form of flakes or bran. The edible excipient may comprise any support that can be consumed by target rodent pests.

Advantageously, the edible excipient comprises at least one food chosen from the group formed from foods of plant origin and foods of animal origin. Advantageously, the edible excipient comprises at least one food chosen to stimulate the appetite of the target rodent pests. In particular, this food is chosen from the group formed from seeds of one or more cereals, hulled seeds of one or more cereals, meals of seeds of one or more cereals, flakes of seeds of one or more cereals, bran of one or more cereals and flour of seeds of one or more cereals. By way of example, the cereals are chosen from the group formed from oat, wheat, barley, corn, soybean and rice.

Advantageously, the food is chosen from the group formed from sweetened foods. For example, they may be foods comprising at least one sugar chosen from the group formed from sucrose, lactose, fructose and glucose. It may be a sugar syrup—for example a sugar syrup obtained by hydrolysis of starch—or a sugar syrup obtained by hydrolysis of sucrose (invert sugar syrup), or a beet sugar syrup, or a maple syrup or a sugarcane syrup, or a syrup obtained from a plant of the *Stevia* genus.

Advantageously, the food is chosen from the group formed from coconut albumen (copra) flakes and flour.

Advantageously, the food is chosen from the group formed from walnuts, hazelnuts and almonds—in grated and/or powder form.

Advantageously, the food is chosen from the group formed from plant fats, plant oils (for example rapeseed oil, soybean fat, sunflower oil, cocoa butter, groundnut oil, groundnut butter, corn oil, palm oil), animal fats and animal oils (butter, lard, fish oil).

Advantageously, the food is chosen from the group formed from proteins of plant origin and proteins of animal origin. By way of example, examples that may be mentioned include powdered milk, especially powdered skimmed milk, eggs, especially powdered eggs, protein hydrolysates of animal origin and protein hydrolysates of plant origin.

Advantageously and according to the invention, the rodenticidal bait is chosen from the group formed from solid baits comprising difethialone and a solid edible excipient. Advantageously, the rodenticidal bait is a solid in divided form, for example in the form of balls or granules. Advantageously, the rodenticidal bait may be a solid in block or paste form that may be consumed by the target rodent pests or a solid material that may be nibbled by the target rodent pests. Advantageously, the solid rodenticidal bait according to the invention may be in the form of a rigid block, a semi-rigid block, a foam, a powder or a gel.

Advantageously, the rodenticidal bait which is in the form of a powder, in the form of a foam or in the form of a gel is suitable for soiling the fur of the target rodent pest(s) and for being ingested by said pests during their grooming.

It may be a solid rodenticidal bait comprising difethialone, with the exclusion of a racemic mixture of the dextrorotatory and laevorotatory enantiomers of said homo-stereoisomer of difethialone. It may also be a solid rodenticidal bait comprising difethialone and in which said hetero-stereoisomer of difethialone is predominantly in laevorotatory enantiomer form. It may also be a solid rodenticidal bait comprising difethialone in which the difethialone is predominantly in the laevorotatory enantiomer form of said hetero-stereoisomer of difethialone.

Advantageously and according to the invention, the rodenticidal bait is chosen from the group formed from liquid baits comprising difethialone and a liquid edible excipient. The rodenticidal bait is then a drink for target rodent pests. It may be a solution of difethialone in a solvent for difethialone, with the exclusion of a racemic mixture of dextrorotatory and laevorotatory enantiomers of said hetero-stereoisomer of difethialone. It may also be a solution of difethialone in a solvent for difethialone and in which said hetero-stereoisomer of difethialone is predominantly in laevorotatory enantiomer form. It may also be a solution of difethialone in a solvent for difethialone and in which the difethialone is predominantly in the laevorotatory enantiomer form of said hetero-stereoisomer of difethialone. It may also be a suspension or an emulsion of difethialone in a liquid medium.

The invention also relates to a rodenticidal bait in which the difethialone is optically active. However, it is not excluded for the difethialone of the rodenticidal bait according to the invention to be optically inactive.

Advantageously, the rodenticidal bait comprises at least one dye. Such a dye makes it possible in particular to give said rodenticidal bait a colour that is readily detectable and identifiable by a person handling the rodenticidal bait.

Advantageously, the rodenticidal bait comprises at least one preserving agent capable of ensuring its conservation during its storage. Advantageously, the rodenticidal bait comprises at least one bittering compound such as denatonium benzoate, also known as Bitrex®, which is intended to reduce the risks of accidental consumption by non-target organisms.

Advantageously, in one particular variant, the composition and the rodenticidal bait according to the invention exclusively comprise difethialone—in which the hetero-stereoisomer is not a racemic mixture—as rodenticidal substance. In particular, the composition and the rodenticidal bait according to the invention are free of any other anticoagulant substance for rodenticidal use.

However, in this variant according to the invention, the composition and the rodenticidal bait may comprise any pest-control substance other than a rodenticide, such as an insecticidal and/or acaricidal substance.

Advantageously, in another particular variant, the composition and the rodenticidal bait according to the invention comprise difethialone with the exclusion of a racemic mixture of laevorotatory and dextrorotatory enantiomers of said hetero-stereoisomer and at least one other substance different from difethialone as rodenticidal substance. This other rodenticidal substance different from difethialone may be another anticoagulant substance—especially of the anti-vitamin K type or not—or another non-anticoagulant rodenticidal substance.

The invention also relates to a process for controlling target rodent pests, in which there is spread an amount of rodenticidal bait comprising:
  at least one excipient that is edible for target rodent pests; and
  the laevorotatory enantiomer of the configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations; with the exclusion of a racemic mixture of laevorotatory and dextrorotatory enantiomers of said hetero-stereoisomer of difethialone, i.e. with the exclusion of a mixture in which the laevorotatory enantiomer of said hetero-stereoisomer of difethialone and the dextrorotatory enantiomer of said hetero-stereoisomer of difethialone are in equal amounts.

The invention also relates to a process for controlling target rodent pests, in which there is spread an amount of rodenticidal bait according to the invention, said amount of bait being sufficient to be rodenticidal.

An amount of rodenticidal bait comprising said hetero-stereoisomer of difethialone predominantly in laevorotatory enantiomer form, which has reduced hepatic persistence in the target rodent pest but sufficient rodenticidal efficacy, is thus spread. The process according to the invention thus makes it possible to limit the secondary poisoning of non-rodent mammals and birds that are liable to feed on poisoned rodents which are dead or alive but comprising a reduced amount—and especially a non-lethal amount—of difethialone. The process according to the invention also makes it possible to limit such secondary poisoning of non-rodent mammals and birds that are liable to preferentially consume the viscera—in particular the liver—of said dead or live poisoned rodents.

Advantageously and according to the invention, said hetero-stereoisomer of difethialone is predominantly in laevorotatory enantiomer form.

Advantageously and according to the invention, the difethialone is predominantly in the laevorotatory enantiomer form of said hetero-stereoisomer of difethialone.

Advantageously and as a variant according to the invention, the following are chosen in combination:
  the edible excipient;
  a proportion of laevorotatory enantiomer of said hetero-stereoisomer of difethialone relative to said hetero-stereoisomer of difethialone;
  a proportion of laevorotatory enantiomer of said hetero-stereoisomer of difethialone relative to the difethialone;
  a mass proportion of difethialone relative to the rodenticidal bait; and
  an amount of spread bait;
so that target rodent pests consume an amount of difethialone that is sufficient to be lethal to said target rodent pests which consume said bait in the course of a single period of 24 consecutive hours.

A rodenticidal bait according to this variant of the invention is a bait that is mortal in a single intake, or a "one-shot" bait. Advantageously and according to this variant of the invention, the mass proportion of difethialone in the rodenticidal bait is between 2 ppm and 200 ppm, especially between 5 ppm and 100 ppm, preferably between 10 ppm and 50 ppm, more preferentially between 15 ppm and 50 ppm.

Advantageously and in another variant according to the invention, the following are chosen in combination:
  the edible excipient;
  a proportion of laevorotatory enantiomer of said hetero-stereoisomer of difethialone relative to said hetero-stereoisomer of difethialone;
  a proportion of laevorotatory enantiomer of said hetero-stereoisomer of difethialone relative to the difethialone;
  a mass proportion of difethialone relative to the rodenticidal bait; and
  an amount of spread bait;
so that target rodent pests consume an amount of difethialone:
  which is non-lethal to target rodent pests, i.e. which is generally non-lethal to target rodent pests which consume said bait over a period of 24 consecutive hours; and
  which is sufficient to be lethal to target rodent pests which consume said bait over several 24-hour periods, said periods being consecutive.

This other variant of the invention is thus also directed towards a process for controlling target rodent pests, in which there is spread an amount of rodenticidal bait that is lethal to target rodent pests durably consuming this rodenticidal bait and non-lethal to non-target rodents or animals accidentally consuming this rodenticidal bait. This is then referred to as a "multi-dose" or "multi-feeding" control process. In such a process according to the invention, the consumption of rodenticidal bait by a target rodent pest over a period of 24 hours is generally insufficient to result in the death of said rodent, whereas repeated consumption of rodenticidal bait over at least two consecutive days results in the death of the target rodent pest.

The invention is thus directed towards a process for controlling a population of target rodent pests, in which target rodent pests are provided with an amount of rodenticidal bait that is liable to be ingested by the target rodent pests, said amount of rodenticidal bait being sufficient to kill target rodent pests which consume said rodenticidal bait over several days.

Advantageously, the amount of rodenticidal bait spread, the mass proportion of difethialone relative to the rodenticidal bait and the proportion of laevorotatory enantiomer of said hetero-stereoisomer of difethialone relative to the difethialone are adapted so that the consumption of the rodenticidal bait is lethal to target rodent pests which daily consume bait over at least two 24-hour periods, especially from 3 to 7 periods, said periods being consecutive.

Advantageously, in this other variant of a process according to the invention, since the proportion of laevorotatory enantiomer of said hetero-stereoisomer of difethialone is greater than 95%—especially about 100%—relative to the difethialone, the mass proportion of difethialone relative to the rodenticidal bait is between 5 ppm and 50 ppm, especially between 10 ppm and 20 ppm, for example about 15 ppm. In a process according to the invention, an amount of rodenticidal bait that is sufficient to satisfy their daily appetite is provided to target rodent pests, said rodenticidal bait comprising a major proportion of laevorotatory enantiomer of said hetero-stereoisomer of difethialone.

In a process according to the invention, the amount of rodenticidal bait spread, the proportion of the laevorotatory enantiomer of said hetero-stereoisomer of difethialone relative to the difethialone and the mass proportion of difethialone relative to the rodenticidal bait are adapted so as to allow consumption of rodenticidal bait for several days by target rodent pests, while at the same time limiting:
- the risks of primary intoxication of non-target mammals and birds which are liable to consume such a rodenticidal bait only occasionally and accidentally;
- the risks of secondary intoxication, for example of predators of target rodents, which are liable to consume target rodents—dead or live—that have ingested an amount of said bait.

The invention also relates to a chromatographic process for obtaining a laevorotatory enantiomer of a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said hetero-stereoisomer have different absolute configurations, in which process:
- a high-pressure liquid chromatography column of dimensions 150×2 mm, and comprising a chiral stationary phase constituted of particles of tris(4-methylbenzoate) cellulose, said particles having a mean size of 3 m and having a mean pore size of 1000 Å, is chosen;
- a mixture formed from acetonitrile (A) and water comprising 0.1% by volume of formic acid (B), with an A/B volume ratio of 80/20 and with a flow rate of the liquid mobile phase in the chromatography column of 0.25 mL/minute, is chosen as liquid mobile phase;
- separation of the configurational stereoisomers of difethialone is performed at room temperature, during which:
  - a liquid composition comprising said laevorotatory enantiomer of said hetero-stereoisomer of difethialone is introduced into the top of the chromatography column; and then
  - the liquid composition is entrained with the mobile phase in the chromatography column under conditions suitable for separating the configurational stereoisomers of difethialone; and
  - a fraction of the mobile phase comprising said laevorotatory enantiomer of said hetero-stereoisomer of difethialone is collected with a retention time $t_2$ having a value such that $t_1 < t_2 < t_3 < t_4$; $t_1$, $t_3$ and $t_4$ representing the retention times of each of the configurational stereoisomers of difethialone different from the laevorotatory enantiomer of said hetero-stereoisomer of difethialone, separately from a dextrorotatory enantiomer of said hetero-stereoisomer of difethialone with a retention time $t_3$ and separately from the laevorotatory and dextrorotatory enantiomers of a configurational stereoisomer of difethialone, named homo-stereoisomer, in which carbons 1 and 3 of the 1,2,3,4-tetrahydronaphthalene group of said homo-stereoisomer have the same absolute configuration, and of retention times $t_1$ and $t_4$; and then
  - the liquid mobile phase of said fraction is removed so as to obtain said laevorotatory enantiomer of said hetero-stereoisomer of difethialone.

The invention also relates to said laevorotatory enantiomer of said hetero-stereoisomer of difethialone obtained via a process according to the invention.

The invention also relates to a configurational stereoisomer of difethialone, to a process for obtaining such a configurational stereoisomer, to a composition and a rodenticidal bait comprising such a configurational stereoisomer and to a process for controlling target rodent pests, characterized in combination by all or some of the characteristics mentioned hereinabove or hereinbelow.

BRIEF DESCRIPTION OF THE FIGURES

Other aims, characteristics and advantages of the invention will emerge on reading the following description and the examples, which are given for purely non-limiting purposes and which refer to the attached figures, in which.

Figure 2:
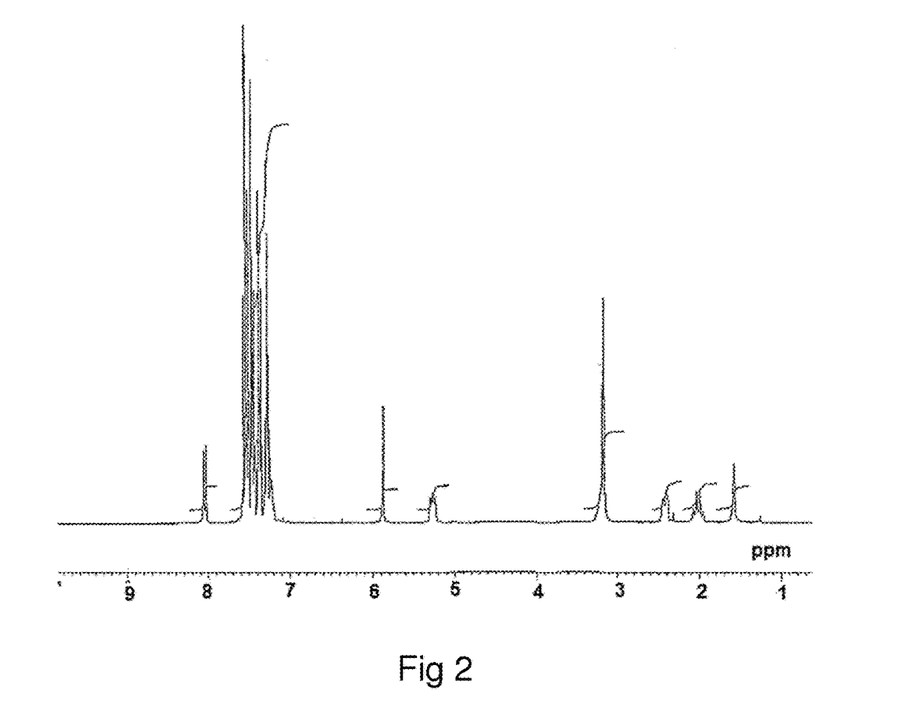
FIG. 2 is a proton NMR spectrum at 300 MHz of said hetero-stereoisomer of difethialone.
Figure 3:
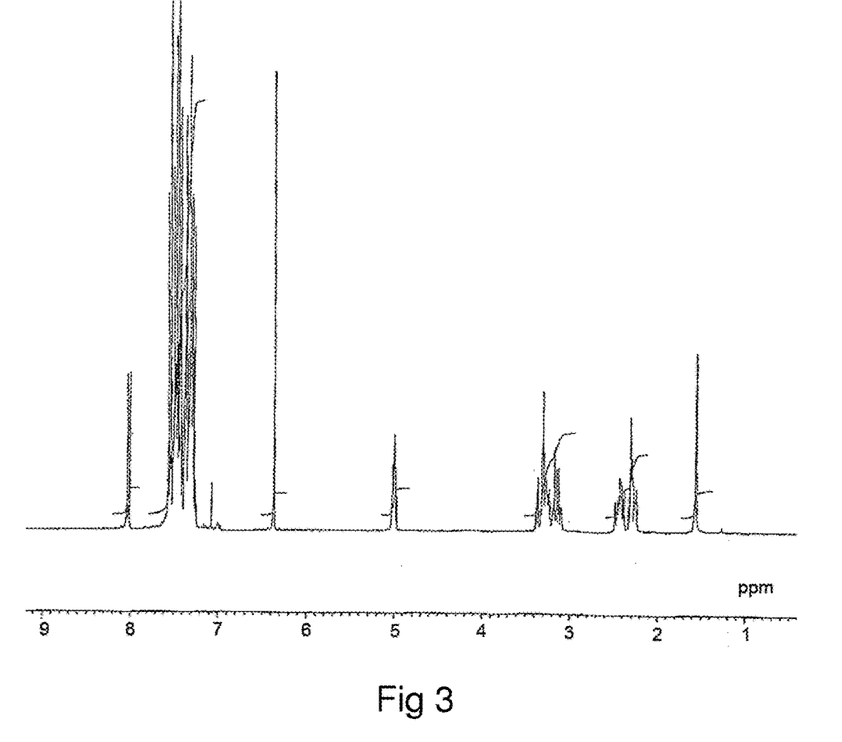
FIG. 3 is a proton NMR spectrum at 300 MHz of said homo-stereoisomer of difethialone.

A. Purification of the Laevorotatory Enantiomer of Said Hetero-stereoisomer of Difethialone A. 1. Identification of Said Hetero-stereoisomer of Difethialone and of Said Homo-stereoisomer of Difethialone Said hetero-stereoisomer of difethialone is identified by proton magnetic resonance ($^1$H-NMR) spectroscopy. Said hetero-stereoisomer of difethialone dissolved in CDCl$_3$ has a signal with a chemical shift (δ) of about 5.3 ppm and corresponding to the proton borne by carbon 1 of the 1,2,3,4-tetrahydronaphthalene group of difethialone as illustrated in FIG. 2. Said hetero-stereoisomer of difethialone is distinguished from said homo-stereoisomer of difethialone, the latter, dissolved in CDCl$_3$, having a multiplet at a chemical shift ($\delta$) of between 4.9 ppm and 5.1 ppm and corresponding to the proton borne by carbon 1 of the 1,2,3,4-tetrahydronaphthalene group of difethialone (FIG. 3).

A.2. Separation of the Laevorotatory and Dextrorotatory Enantiomers of Said Hetero-Stereoisomer of Difethialone by High-Pressure Liquid Chromatography on a Chiral Column The inventors solved the complex and hitherto unresolved problem of separating the enantiomers of difethialone and in particular the laevorotatory and dextrorotatory enantiomers of said hetero-stereoisomer of difethialone. They succeeded in separating the enantiomers of said hetero-stereoisomer of difethialone and in preparing the dextrorotatory enantiomer of said hetero-stereoisomer of difethialone by high-pressure (high-performance) liquid chromatography on a LUX® Cellulose-3 chiral column (Phenomenex, Le Pecq, France) of dimensions 150×2 mm and comprising a chiral stationary phase constituted of porous particles of tris(4-methylbenzoate) cellulose, with a particle size of 3 μm and a porosity of 1000 Å. The mobile phase used is an eluent formed from a mixture of acetonitrile (A) and water comprising formic acid in a volume proportion of 0.1% in the water (B) with an A/B volume ratio of 80/20. The flow rate of the mobile phase in the column is 0.25 mL/minute and the separation is performed at a temperature of 23.2° C. The solution containing the sample to be analysed is at a concentration of 1 μg of difethialone per millilitre in acetonitrile and is filtered through a regenerated cellulose membrane with a cut-off threshold of 0.2 μm. The volume of solution containing the sample to be analysed injected onto the column is 1 μL.

Figure 1:
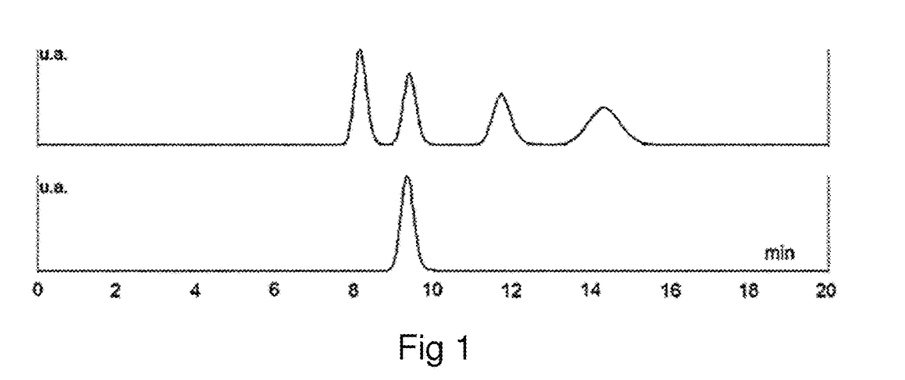
FIG. 1 represents a chromatogram of separation of the enantiomers of difethialone (top) and a chromatogram of analysis of the laevorotatory enantiomer of said hetero-stereoisomer of difethialone (bottom) by high-pressure liquid chromatography on a chiral column.

In a process for separating the enantiomers of said hetero-stereoisomer of difethialone, it is possible to detect said enantiomers leaving the high-pressure liquid chromatography column by tandem mass spectrometry (MS/MS) in negative electrospray ionization mode (ESI: ElectroSpray Ionization). The temperature of the nebulizer gas is 350° C. and its flow rate is 8 L/minute. The pressure of the nebulizer gas is brought to 2700 hPa. In particular, the MRM ("Multiple Reaction Monitoring") transitions m/z 537.1→151.0 and m/z 537.1→78.99, corresponding to the difethialone signals, are detected. FIG. 1 represents the chromatograms of difethialone (top) and of the laevorotatory enantiomer of the isolated hetero-stereoisomer of difethialone (bottom).

Under these conditions, the value of the retention time ($t_2$) for the laevorotatory enantiomer of said hetero-stereoisomer of difethialone according to the invention is about 9.4 minutes as described in FIG. 1, and the value of the retention time ($t_3$) for the dextrorotatory enantiomer of said hetero-stereoisomer of difethialone is about 11.7 minutes, such that the dextrorotatory and laevorotatory enantiomers of said hetero-stereoisomer may be separated by high-pressure liquid chromatography on a chiral column.

Under these same conditions, the value of the retention time ($t_4$) for said dextrorotatory enantiomer of said homo-stereoisomer according to the invention is about 14.4 minutes, and the value of the retention time ($t_1$) for the laevorotatory enantiomer of said homo-stereoisomer is about 8.1 minutes, such that the dextrorotatory and laevorotatory enantiomers of said homo-stereoisomer may also be separated by high-pressure liquid chromatography on a chiral column. Thus, under these conditions, the order of elution of the enantiomers of difethialone is such that $t_1 < t_2 < t_3 < t_4$.

It is possible under these experimental conditions (stationary phase, mobile phase, temperature) to perform a preparative separation of the laevorotatory and dextrorotatory enantiomers of said hetero-stereoisomer of difethialone by using a similar stationary phase with a particle size of greater than 3 m, and a chromatography column of larger dimensions, especially a diameter of 20 mm.

B. Structural Characterization

B.1. UV Spectroscopy

The UV spectrum of the laevorotatory enantiomer of said hetero-stereoisomer of difethialone dissolved in chloroform (CHCl$_3$) shows an absorbance peak centred at 238.2 nm and an absorbance peak centred at 259.5 nm.

B.2. Optical Rotation

The inventors characterized the laevorotatory enantiomer of said hetero-stereoisomer of difethialone in isolated form by means of its optical rotation (also known as the optical activity or circular birefringence), i.e. its ability to deviate the polarization plane of polarized light. Deviation of the polarization plane of polarized light clockwise facing the polarized light beam characterizes a dextrorotatory solution, and deviation of the polarization plane of polarized light anticlockwise facing the polarized light beam characterizes a laevorotatory solution and compound.

The optical rotation of a solution of laevorotatory enantiomer of said hetero-stereoisomer of difethialone in chloroform (CHCl$_3$) is measured at a concentration of 6.95 g/L. The optical rotation of this solution is measured by means of a P 2000 digital polarimeter (JASCO, Bouguenais, France) operating with excitatory light with a wavelength of 589 nm. The mean optical rotation a obtained on two series of ten measurements is −0.904°. The specific optical rotation at 25° C. $[\alpha]^{25°\ C.}_{589nm}$ for the laevorotatory enantiomer of said hetero-stereoisomer of difethialone dissolved in chloroform, measured on the sodium D line (589 nm), is −13°.

B.3. Circular Dichroism

Figure 7:
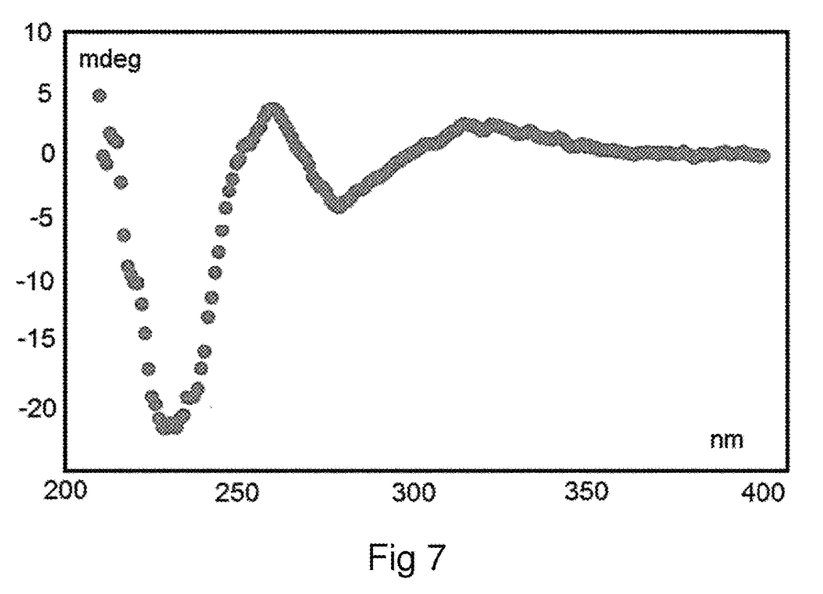
FIG. 7 is a circular dichroism spectrum of the laevorotatory enantiomer of said hetero-stereoisomer of difethialone.

The circular dichroism spectrum of the isolated laevorotatory enantiomer of said hetero-stereoisomer of difethialone reflects the difference in absorbance ($\Delta A = A_L - A_R$) of the two waves of left circular polarization (LCP) of intensity $A_L$ and of right circular polarization (RCP) of intensity $A_R$. This makes it possible to distinguish the dextrorotatory and laevorotatory enantiomers of said homo-stereoisomer of difethialone. This difference in absorbance of the two circularly polarized waves is measured in a J-815 circular dichroism spectrometer (JASCO, Bouguenais, France). 2 mL of a solution of laevorotatory enantiomer of said hetero-stereoisomer of difethialone in methanol (CH$_3$OH) at a concentration of 0.94 mg/mL are prepared. The solution is transferred into a quartz spectrophotometer cuvette. The circular dichroism spectrum of the solution is measured at 25° C. between 200 nm and 400 nm. The circular dichroism spectrum of the laevorotatory enantiomer of said hetero-stereoisomer of difethialone measured under these conditions is shown in FIG. 7. The circular dichroism value is negative between the wavelengths of between 225 nm and 250 nm.

B.4. Nuclear Magnetic Resonance

The proton nuclear magnetic resonance ($^1$H-NMR) spectrum at 300 MHz of the hetero-stereoisomer of difethialone in CDCl$_3$ (FIG. 2) has a multiplet whose chemical shift ($\delta$) is about 5.3 ppm. The proton nuclear magnetic resonance spectrum at 300 MHz of the homo-stereoisomer of difethialone in CDCl$_3$ (FIG. 3) has a multiplet whose chemical shift ($\delta$) is between 4.9 ppm and 5.1 ppm, corresponding to carbon 1 of the 1,2,3,4-tetrahydronaphthalene group of said homo-stereoisomer of difethialone. The proton NMR spectra of the dextrorotatory and laevorotatory enantiomers of said hetero-stereoisomer of difethialone are indistinguishable from each other.

Figure 4:
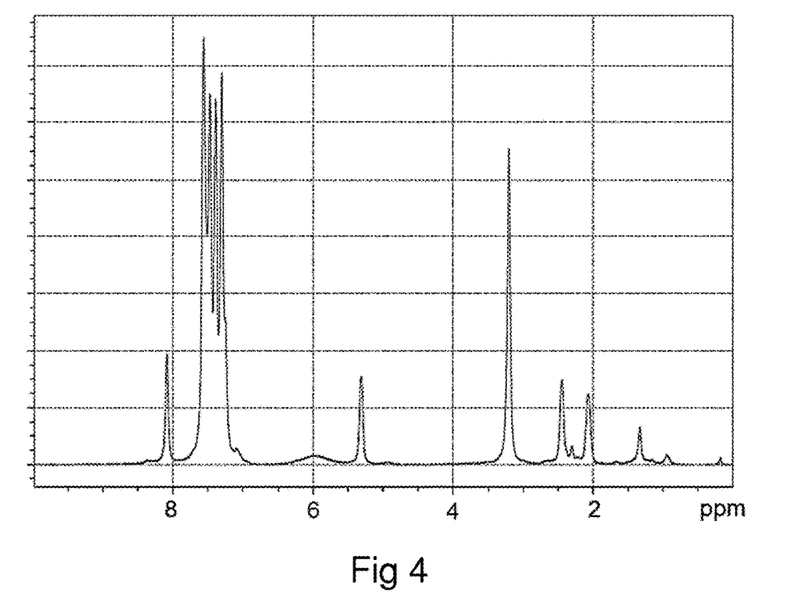
FIG. 4 is a proton NMR spectrum at 500 MHz of the laevorotatory enantiomer of said hetero-stereoisomer of difethialone according to the invention.

FIG. 4 is a proton NMR ($^1$H-NMR) spectrum of the laevorotatory enantiomer of said hetero-stereoisomer of difethialone dissolved at a concentration of 40 mg/mL in CDCl$_3$, having a multiplet whose chemical shift (δ) is about 5.3 ppm, characteristic of said hetero-stereoisomer of difethialone.

Figure 5:
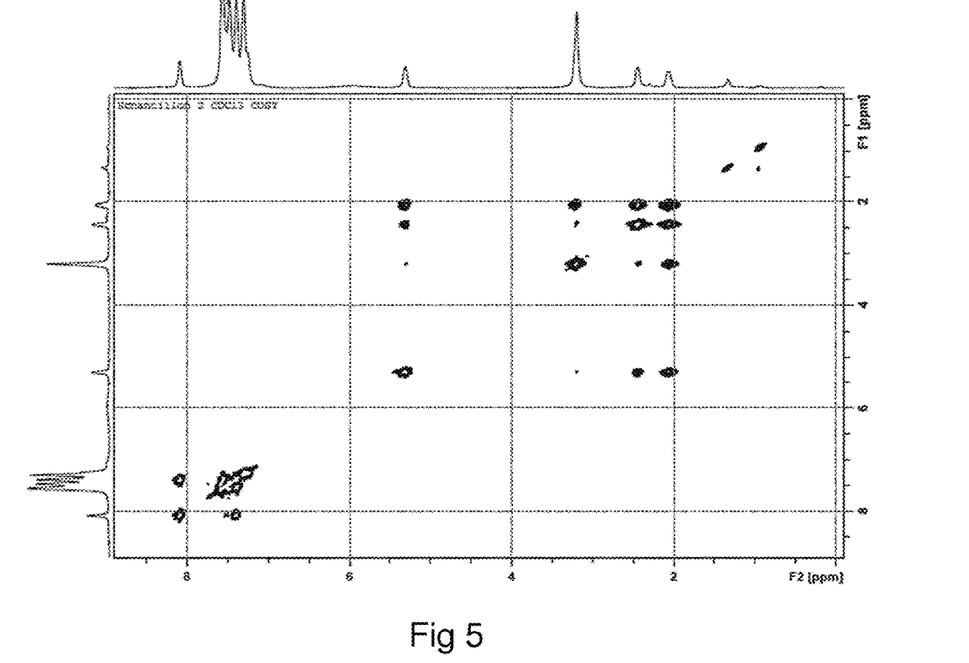
FIG. 5 is an analysis by proton NMR ($^1$H-NMR) correlation spectroscopy at 500 MHz of the laevorotatory enantiomer of said hetero-stereoisomer of difethialone.

FIG. 5 is a two-dimensional proton NMR (2D $^1$H-NMR) spectrum obtained by correlation spectroscopy of the laevorotatory enantiomer of said hetero-stereoisomer of difethialone dissolved at a concentration of 40 mg/mL in CDCl$_3$, acquired on a Brüker Avance III HD spectrometer (500 MHz) equipped with a Prodigy motorized multi-core direct cryoprobe. It allows identification of the coupling of the proton borne by carbon 1 of the 1,2,3,4-tetrahydronaphthalene group of said homo-stereoisomer of difethialone (5.3 ppm) with the protons borne by carbon 2 of the 1,2,3,4-tetrahydronaphthalene group at 2.0 and 2.4 ppm.

Figure 6:
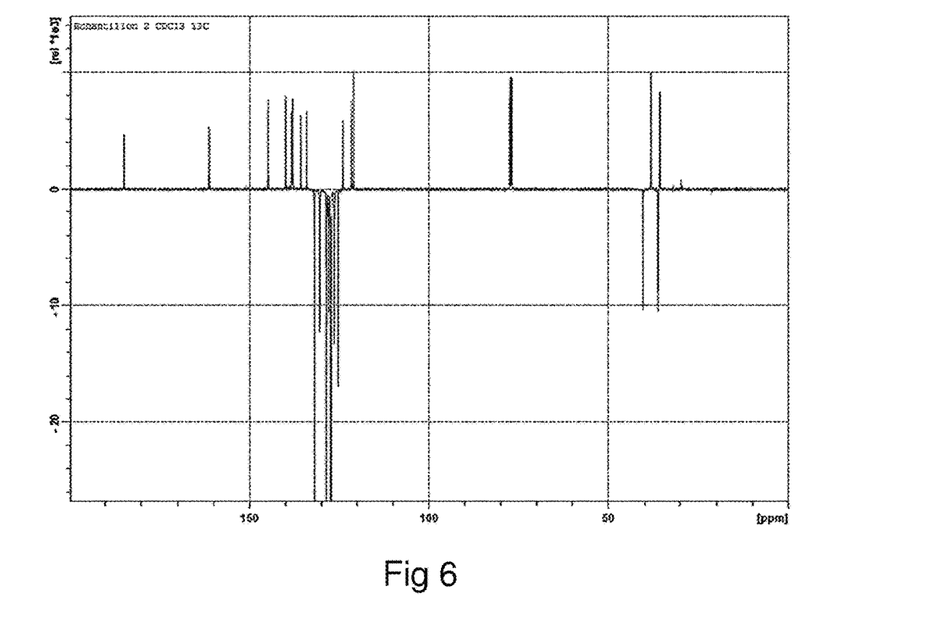
FIG. 6 is a $^{13}$C carbon NMR spectrum at 500 MHz of the laevorotatory enantiomer of said hetero-stereoisomer of difethialone.

FIG. 6 is a $^{13}$C NMR spectrum of the laevorotatory enantiomer of said hetero-stereoisomer of difethialone dissolved in CDCl$_3$ at a concentration of 40 mg/mL, acquired on a Brüker Avance III HD spectrometer (500 MHz) equipped with a Prodigy motorized multi-core direct cryoprobe. It allows identification of the 31 carbon atoms of difethialone. The $^{13}$C-NMR spectrum of the laevorotatory enantiomer of said hetero-stereoisomer of difethialone is not distinguished from the $^{13}$C-NMR spectrum of the dextrorotatory enantiomer of said hetero-stereoisomer of difethialone. However, said hetero-stereoisomer of difethialone has a signal at a chemical shift of about 38.2 ppm and a signal at a chemical shift of about 40.3 ppm, which are characteristic of and distinctive for said homo-stereoisomer of difethialone.

C. Extraction Of Difethialone from the Liver of Rats Treated with Difethialone for the Purpose of Analysis of the Various Enantiomers of Difethialone C.1. Homogenization of the Liver Sample About 0.525 g (±0.025 g) of rat liver is weighed out accurately and placed in a 50 mL polypropylene tube. 10 mL of acetone are added and the suspension is homogenized using an Ultra-Turrax® homogenizer/disperser for a time of about 30 seconds. The homogenizer/disperser shaft is rinsed with hot water and then twice with 20 mL of acetone in a polypropylene tube. The homogenate is centrifuged for 5 minutes at a centrifugation speed of 3000 rpm (revolutions per minute). The supernatant is collected and transferred into a test tube. The sample is subjected to evaporation under a stream of nitrogen (N$_2$) at a temperature of 40° C. so as to form a dry extract.

C.2. Lipid Removal 1 mL of acetonitrile is added to the tube containing the dry extract so as to dissolve it. The acetonitrile solution is washed twice successively with 1 mL of hexane. The lipid-free extract is dried under a stream of nitrogen (N$_2$) at a temperature of 40° C. and is then taken up in 0.5 mL of methanol and dissolved by vortex stirring. 0.5 mL of ultra-pure (Milli-Q) water is then added. The sample is vortex-homogenized.

C.3. Solid-phase Extraction (SPE) of Difethialone 1 mL of dichloromethane (CH$_2$Cl$_2$), then 1 mL of methanol (CH$_3$OH), then 1 mL of ultra-pure (Milli-Q) water are passed through an Oasis HLB 1 cc cartridge (WAT094225, Waters). The lipid-free liver extract (1 mL MeOH/Milli-Q H$_2$O) containing difethialone is then loaded onto the top of the preconditioned cartridge. The liver extract penetrates through the cartridge by gravity on contact with the solid phase of the cartridge. 1 mL of washing solution formed from methanol (CH$_3$OH) and ultra-pure water (H$_2$O) in a 90/10 volume proportion is then loaded onto the top of the cartridge. The cartridge is dried by suction under vacuum connected to the bottom of the cartridge. 1 mL of eluting solution formed from dichloromethane (CH$_2$Cl$_2$) and methanol (CH$_3$OH) in a 90/10 volume proportion is then loaded onto the top of the cartridge and an eluate comprising difethialone is collected at the bottom of the cartridge. The solvent of the eluate is evaporated off under a stream of nitrogen (N$_2$) at a temperature of 40° C. The sample is taken up in 0.5 mL of acetonitrile (N≡CCH$_3$) and the acetonitrile solution containing difethialone is filtered through a 0.2 μm filter.

C.4. Analysis

The acetonitrile solution containing difethialone is analysed by high-pressure liquid chromatography on a LUX® Cellulose-3 chiral column (Phenomenex, Le Pecq, France) (150×2 mm, particle size of 3 μm) as described in point A2) above.

D. Persistence of the Configurational Stereoisomers of Difethialone in Rat Liver A solution of a mixture of said homo-stereoisomer and of said hetero-stereoisomer of difethialone in a mixture of vegetable oil and 5% DMSO is administered by tube-feeding ("per os") to male and female coumaphen-sensitive rats (*Rattus norvegicus*). The molar proportion of said homo-stereoisomer is 40% and the molar proportion of said hetero-stereoisomer is 60%. Each configurational stereoisomer of difethialone is formed from a racemic mixture of the two laevorotatory and dextrorotatory enantiomers of said corresponding configurational stereoisomer. The solution comprising 40% of said homo-stereoisomer and 60% of said hetero-stereoisomer is administered (on D0) so that the amount of difethialone ingested by each rat is about 3.4 mg per kilogram of rat. To avoid haemorrhage, the tube-fed rats are treated daily by subcutaneous administration of a dose of vitamin K1 (as haemorrhage antidote) at a rate of 0.1 U per 200 g of live rat weight.

At 4 hours (H+4), 9 hours (H+9), 24 hours (H+24), 120 hours (H+120), 168 hours (H+168) and 216 hours (H+216) after tube-feeding, six rats (three male rats and three female rats) anaesthetized beforehand with isoflurane are euthanized, the liver of the euthanized rats is removed, the difethialone is then extracted from the liver and the amount of each configurational stereoisomer of difethialone is assayed via analysis by high-pressure liquid chromatography on a chiral column according to the process described above, the area under the peaks in the chromatogram obtained is measured and each enantiomer is quantified by comparison with a calibration curve. The following are assayed:

the dextrorotatory enantiomer of said homo-stereoisomer;
the laevorotatory enantiomer of said homo-stereoisomer;
the dextrorotatory enantiomer of said hetero-stereoisomer;
the laevorotatory enantiomer of said hetero-stereoisomer;
present in the liver of the tube-fed rats.

The results of the analysis of the content (expressed as nanograms of enantiomer per gram of liver (ng/g)) of each enantiomer of said hetero-stereoisomer of difethialone and of said homo-stereoisomer of difethialone in the liver of the rats as a function of the time (in hours) after the tube-feeding of the rats are given in table 1 below.

TABLE 1

| Time after tube-feeding, hours | Hepatic content, ng/g Total difethialone | | |
|---|---|---|---|
| | | Hetero-stereoisomer | |
| | Homo-stereoisomer | DFN-Hetero-dextro | DFN-Hetero-laevo |
| 4 | 10258.5 | 10589.5 | 5380.5 |
| 9 | 11833.5 | 12155.5 | 5869.5 |
| 24 | 5647 | 8102 | 3613.5 |
| 48 | 4594.5 | 7974.5 | 2804 |
| 120 | 2279.5 | 5431.5 | 1211 |
| 168 | 1007.5 | 3011 | 392.5 |
| 216 | 1301.5 | 4030.5 | 545 |

Figure 8:
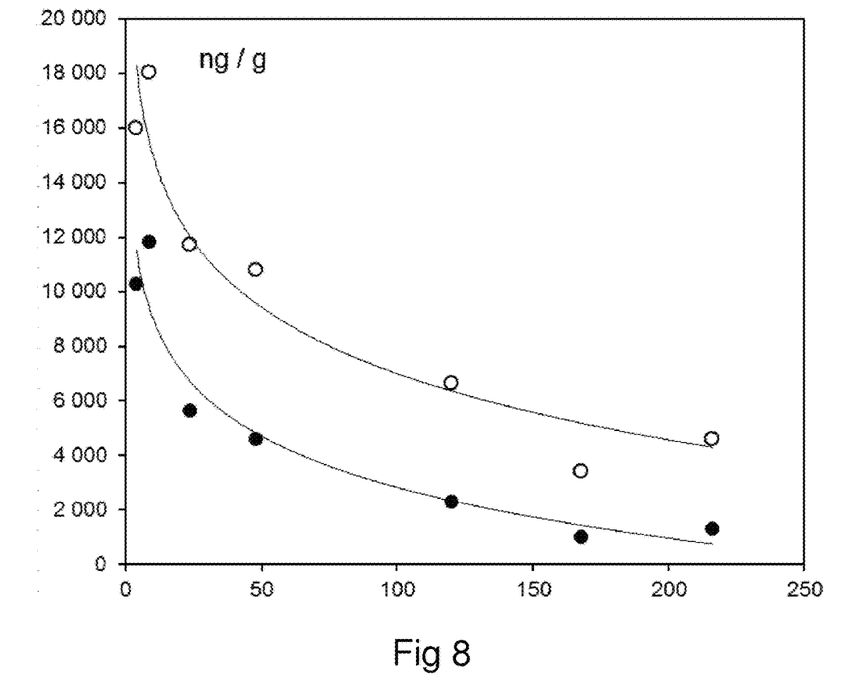
FIG. 8 is a representation in graph form of the change over time of the mean concentration measured in the liver of rats (5 male rats and 5 female rats) of said homo-stereoisomer (●) and of said hetero-stereoisomer (○)

The results of the analysis of the content of said homo-stereoisomer of difethialone and of said hetero-stereoisomer of difethialone are deduced from table 1 and shown in FIG. 8. Said hetero-stereoisomer (○) has hepatic persistence of a higher value than the value of the hepatic persistence of said homo-stereoisomer (●). Now, the inventors also observed that the laevorotatory enantiomer of said hetero-stereoisomer (said hetero-stereoisomer being the most persistent stereoisomer of difethialone) in fact has low hepatic persistence, giving it surprising properties for protection of the environment and of wild animals—for example foxes or birds—which prey on target rodent pests which have consumed the rodenticidal bait or which carrion-feed on the dead bodies of poisoned target rodent pests.

Figure 9:
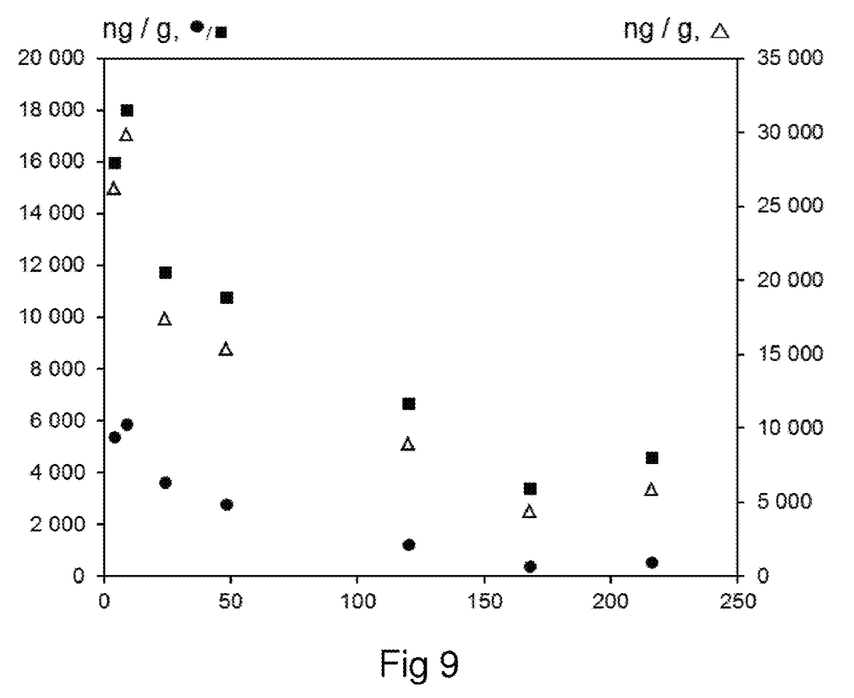
FIG. 9 is a comparative representation in graph form of the change over time of the concentration in the liver of rats of the laevorotatory enantiomer of said hetero-stereoisomer of difethialone (●), of said hetero-stereoisomer of difethialone (■) and of the total difethialone (Δ).

FIG. 9 describes the change over time of the content of the laevorotatory enantiomer of said hetero-stereoisomer of difethialone in the liver, represented by filled circles (●), of the content of said hetero-stereoisomer in the liver, represented by filled squares (■) and of the content of total difethialone in the liver, represented (right-hand scale) by empty triangles (Δ).

The mean content of the laevorotatory enantiomer of said hetero-stereoisomer of difethialone, representing about 30% of the total starting difethialone ingested by the rats, decreases rapidly in the liver of the sacrificed rats. This decrease is faster than the decrease of the dextrorotatory enantiomer of said hetero-stereoisomer of difethialone (not shown in FIG. 9), faster than the decrease of said hetero-stereoisomer of difethialone and faster than the decrease of the total difethialone. The laevorotatory enantiomer of said hetero-stereoisomer of difethialone has significantly lower hepatic persistence than that of the dextrorotatory enantiomer of said hetero-stereoisomer of difethialone, but also than that of the laevorotatory enantiomer of said homo-stereoisomer (less persistent stereoisomer) of difethialone in male rats.

E. Rodenticidal Bait Comprising a Proportion of 11.85 Ppm of Difethialone

A pasty rodenticidal bait according to the invention is prepared by dispersing an amount of laevorotatory enantiomer of said hetero-stereoisomer of difethialone in an edible excipient comprising vegetable fat and cereal flour. The measured proportion of difethialone relative to the bait is 11.8 ppm (11.81 mg of laevorotatory enantiomer of said hetero-stereoisomer of difethialone per kilogram of bait). The proportion of laevorotatory enantiomer of said hetero-stereoisomer relative to the difethialone is 99.7%.

On D0, ten coumaphen-sensitive Sprague-Dawley rats (five male and five female SD rats) are placed in individual cages with a rodenticide-free reference feed. On D3, each rat is weighed, and 50 g of rodenticidal bait as described above are then provided to each rat. This provision of 50 g of rodenticidal bait is renewed daily. The bait consumed by the rats is made up to 50 g of bait on D4, D5 and D6. Starting from D7, the residual rodenticidal baits are removed and rodenticide-free feed is provided to all the rats. The rats are monitored for 3 weeks.

The mean amounts of bait consumed daily by a rat at D4, D5, D6 and D7 expressed in grams per day are given in table 2 below.

TABLE 2

| Bait consumed, g | Mean | Standard deviation |
|---|---|---|
| D4 | 13.2 | 3.6 |
| D5 | 12.7 | 4.6 |
| D6 | 14.7 | 3.5 |
| D7 | 12.1 | 2.4 |

It should be noted that no rat consumed a daily amount of bait of less than 1 g/day. The mean daily consumption of bait relative to the mean mass of the rats over the period from D4 to D7 is 64.7 g of bait per kilogram of rat. Nine out of ten rats die between D9 and D12. The mortality of the bait is 90% on D12.

The hepatic content of the laevorotatory enantiomer of said hetero-stereoisomer of difethialone in each of the rats which die between D9 and D10 is measured by high-pressure liquid chromatography analysis on a chiral column. The values, expressed as micrograms of laevorotatory enantiomer of said hetero-stereoisomer ("DFN-Hetero-laevo") per gram of liver, are given in table 3 below.

TABLE 3

| Hepatic content, μg/g | "DFN-Hetero-laevo", μg/g | Total difethialone, μg/g |
|---|---|---|
| Mean | 11.2 | 11.3 |
| Standard deviation | 4.8 | 0.48 |

The bait containing an 11.81 ppm dose of laevorotatory enantiomer of said hetero-stereoisomer of difethialone makes it possible to obtain a mortality rate of about 90% while minimizing the risks of secondary intoxication of animals—especially birds—which prey or carrion-feed on weakened target rodent pests that have consumed a rodenticidal bait.

It goes without saying that the invention may be the subject of numerous implementation variants and applications. In particular, a composition, a rodenticidal bait and a process for controlling target rodent pests are subject to an infinite number of variants both in the formulation of the bait and in the embodiments of the process.

The invention claimed is:

1. Laevorotatory enantiomer of a configurational stereoisomer of difethialone, named hetero-stereoisomer, the formula of which is 3-(4'-bromobiphenyl-4-yl)-1-(4-hydroxy-thiocoumarin-3-yl)-1,2,3,4-tetrahydronaphthalene, in which carbons 1 and 3 of the 1,2,3,4-tetrahydronaphthalene group have different absolute configurations, said laevorotatory enantiomer of said hereto-stereoisomer of difethialone being in isolated form.

2. Composition comprising the laevorotatory enantiomer of the configurational stereoisomer of difethialone, named hetero-stereoisomer, the formula of which is 3-(4 -bromo-biphenyl-4-yl)-1-(4-hydroxythiocoumarin-3-y;)-1,2,3,4-tetrahydronaphthalene, in which carbons 1 and 3 of the 1,2,3, 4-tetrahydronaphthalene group have different absolute configurations, with the exclusion of a racemic mixture of laevorotatory and dextrorotatory enantiomers of said hetero-stereoisomer of difethialone.

3. Composition according to claim 2, wherein said hetero-stereoisomer is predominantly in laevorotatory enantiomer form.

4. Composition according to claim 2, wherein the difethialone is predominantly in the laevorotatory enantiomer form of said hetero-stereoisomer of difethialone.

5. Composition according to claim 2, comprising an amount of the laevorotatory enantiomer of said hetero-stereoisomer of difethialone such that the ratio of this amount to the amount of difethialone is greater than 25%.

6. Composition according to claim 2, comprising an amount of the laevorotatory enantiomer of said hetero-stereoisomer of difethialone such that the ratio of this amount to the amount of difethialone is greater than 97% in the composition.

7. Rodenticidal bait comprising a composition according to claim 2 and at least one excipient that is edible for target rodent pests.

8. Bait according to claim 7, wherein the edible excipient comprises at least one food chosen from the group formed from cereal seeds, cereal seed meals, cereal seed flours, cereal seed flakes, cereal bran and non-cereal seeds.

9. Bait according to claim 7, comprising a mass amount of difethialone such that the ratio of this mass amount of difethialone to the mass amount of rodenticidal bait is less than 200 ppm.

10. Process for controlling target rodent pests, in which there is spread an amount of bait comprising:
at least one excipient that is edible for target rodent pests; and
the laevorotatory enantiomer of the configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations;
with the exclusion of a racemic mixture of the laevorotatory and dextrorotatory enantiomers of said hetero-stereoisomer of difethialone.

11. Process according to claim 10, wherein said hetero-stereoisomer of difethialone is predominantly in laevorotatory enantiomer form.

12. Process according to claim 10, wherein the difethialone is predominantly in the laevorotatory enantiomer form of said hetero-stereoisomer of difethialone.

13. Process according to claim 10, wherein the following are chosen in combination:
the edible excipient;
a proportion of laevorotatory enantiomer of said hetero-stereoisomer of difethialone relative to said hetero-stereoisomer of difethialone;
a proportion of laevorotatory enantiomer of said hetero-stereoisomer of difethialone relative to the difethialone;
a mass proportion of difethialone relative to the rodenticidal bait; and
an amount of spread bait;
so that target rodent pests consume an amount of difethialone that is sufficient to be lethal to said target rodent pests which consume said bait in the course of a single period of 24 consecutive hours.

14. Process according to claim 10, wherein the following are chosen in combination:
the edible excipient;
a proportion of laevorotatory enantiomer of said hetero-stereoisomer of difethialone relative to said hetero-stereoisomer of difethialone;
a proportion of laevorotatory enantiomer of said hetero-stereoisomer of difethialone relative to the difethialone;
a mass proportion of difethialone relative to the rodenticidal bait; and
an amount of spread bait;
so that target rodent pests consume an amount of difethialone:
which is non-lethal to target rodent pests which consume said bait over a period of 24 consecutive hours; and
which is sufficient to be lethal to target rodent pests which consume said bait over several 24-hour periods, said periods being consecutive.

15. Chromatographic process for obtaining a laevorotatory enantiomer of a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said hetero-stereoisomer have different absolute configurations, in which process:
a high-pressure liquid chromatography column of dimensions 150×2 mm, and comprising a chiral stationary phase constituted of particles of tris(4-methylbenzoate) cellulose, said particles having a mean size of 3 µm and having a mean pore size of 1000 Å, is chosen;
a mixture formed from acetonitrile (A) and water comprising 0.1% by volume of formic acid (B), with an A/B volume ratio of 80/20 and with a flow rate of the liquid mobile phase in the chromatography column of 0.25 mL/minute, is chosen as liquid mobile phase;
separation of the configurational stereoisomers of difethialone is performed at room temperature, during which:
a liquid composition comprising said laevorotatory enantiomer of said hetero-stereoisomer of difethialone is introduced into the top of the chromatography column; and then
the liquid composition is entrained with the mobile phase in the chromatography column under conditions suitable for separating the configurational stereoisomers of difethialone; and
a fraction of the mobile phase comprising said laevorotatory enantiomer of said hetero-stereoisomer of difethialone is collected with a retention time $t_2$ having a value such that $t_1 < t_2 < t_3 < t_4$; $t_1$, $t_3$ and $t_4$ representing the retention times of each of the configurational stereoisomers of difethialone different from the laevorotatory enantiomer of said hetero-stereoisomer of difethialone, separately from a dextrorotatory enantiomer of said hetero-stereoisomer of difethialone with a retention time $t_3$ and separately from the laevorotatory and dextrorotatory enantiomers of a configurational stereoisomer of difethialone, named homo-stereoisomer, in which carbons 1 and 3 of the 1,2,3,4-tetrahydronaphthalene group of said homo-stereoisomer have the same absolute configuration, and of retention times $t_1$ and $t_4$; and then
the liquid mobile phase of said fraction is removed so as to obtain said laevorotatory enantiomer of said hetero-stereoisomer of difethialone.

16. Composition according to claim 3, wherein the difethialone is predominantly in the laevorotatory enantiomer form of said hetero-stereoisomer of difethialone.

17. Composition according to claim 3, comprising an amount of the laevorotatory enantiomer of said hetero-stereoisomer of difethialone such that the ratio of this amount to the amount of difethialone is greater than 25%.

18. Composition according to claim 4, comprising an amount of the laevorotatory enantiomer of said hetero-stereoisomer of difethialone such that the ratio of this amount to the amount of difethialone is greater than 25%.

19. Composition according to claim 3, comprising an amount of the laevorotatory enantiomer of said hetero-stereoisomer of difethialone such that the ratio of this amount to the amount of difethialone is greater than 97% in the composition.

20. Composition according to claim 4, comprising an amount of the laevorotatory enantiomer of said hetero-stereoisomer of difethialone such that the ratio of this amount to the amount of difethialone is greater than 97% in the composition.

\* \* \* \* \*

UNITED STATES PATENT AND TRADEMARK OFFICE
CERTIFICATE OF CORRECTION

PATENT NO. : 10,501,434 B2
APPLICATION NO. : 16/061084
DATED : December 10, 2019
INVENTOR(S) : Hervé Caruel et al.

It is certified that error appears in the above-identified patent and that said Letters Patent is hereby corrected as shown below:

In the Claims

Column 20, Claim 2, Line 66: The formula after the "3-" is currently listed as:
"(4- bromobiphenyl-4-yl)-1-(4-hydroxythiocoumarin-3-y;)"
It should read:
"(4'-bromobiphenyl-4-yl)-1-(4-hydroxythiocoumarin-3-y1)"

Signed and Sealed this
Eighteenth Day of February, 2020

Andrei Iancu
*Director of the United States Patent and Trademark Office*